(12) United States Patent
Shannon et al.

(10) Patent No.: US 6,994,666 B2
(45) Date of Patent: Feb. 7, 2006

(54) NON-POROUS SMOOTH VENTRICULAR ASSIST DEVICE CONDUIT

(75) Inventors: Donald T. Shannon, Trabuco Canyon, CA (US); Chris C. Kuo, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/874,846

(22) Filed: Jun. 5, 2001

(65) Prior Publication Data

US 2002/0183584 A1    Dec. 5, 2002

(51) Int. Cl.
*A61M 5/00* (2006.01)
*A61N 1/362* (2006.01)
*A61F 2/06* (2006.01)

(52) U.S. Cl. .............. 600/16; 604/8; 623/1.44
(58) Field of Classification Search ............ 610/16–18; 604/8; 623/1.44, 1.45, 1.39, 155; D24/155; 206/363, 364, 370; 600/16–18
See application file for complete search history.

(56) References Cited

U.S. PATENT DOCUMENTS

| | | | | |
|---|---|---|---|---|
| 3,843,974 A | * | 10/1974 | Miller et al. ................ | 623/3.29 |
| 4,011,947 A | * | 3/1977 | Sawyer ........................ | 206/363 |
| 4,086,665 A | | 5/1978 | Poirier | |
| 4,844,259 A | * | 7/1989 | Glowczewskie et al. .... | 206/370 |
| 4,955,899 A | | 9/1990 | Della Corna et al. | |
| 5,061,276 A | * | 10/1991 | Tu et al. .................... | 623/1.33 |
| 5,246,452 A | * | 9/1993 | Sinnott ....................... | 623/1.23 |
| 5,354,329 A | * | 10/1994 | Whalen ....................... | 623/1.44 |
| 5,615,770 A | * | 4/1997 | Applebaum et al. ......... | 206/363 |
| 5,800,512 A | | 9/1998 | Lentz et al. | |
| 5,824,050 A | | 10/1998 | Karwoski et al. | |
| 5,843,171 A | * | 12/1998 | Campbell et al. ........... | 606/198 |
| 5,876,386 A | * | 3/1999 | Samson ...................... | 604/524 |
| 5,972,441 A | * | 10/1999 | Campbell et al. .......... | 428/34.1 |
| 5,976,192 A | * | 11/1999 | McIntyre et al. ............. | 600/36 |
| 6,001,056 A | | 12/1999 | Jassawalla et al. | |
| 6,007,478 A | * | 12/1999 | Siess et al. .................... | 600/16 |
| 6,053,943 A | * | 4/2000 | Edwin et al. ............... | 623/1.25 |
| 6,056,723 A | * | 5/2000 | Donlon .................. | 604/102.01 |
| 6,102,845 A | * | 8/2000 | Woodard et al. .............. | 600/16 |
| 6,423,031 B1 | * | 7/2002 | Donlon .................. | 604/102.01 |

FOREIGN PATENT DOCUMENTS

EP    1 016 384    7/2000

* cited by examiner

Primary Examiner—Jeffrey R. Jastrzab
(74) Attorney, Agent, or Firm—Rajiv Yadav; Guy L. Cumberbatch

(57) ABSTRACT

An improved inflow conduit for an implantable ventricular assist device comprising covering the flexible porous tubular graft body of the conduit with an attached non-porous polymer to produce a non-porous conduit. The flexible conduit has an upstream end and a downstream end, a ventricular attachment structure to which the upstream end of the body connects; and a coupling fitting on the downstream end of the body. Also taught is a combination of the improved inflow conduit with an implantable ventricular assist device. A method for the treatment of congestive heart failure, comprising implanting the implantable ventricular assist device in a patient in need of such treatment, as well as an article of manufacture, comprising packaging material and the implantable ventricular assist device contained within the packaging material are also provided.

27 Claims, 3 Drawing Sheets

NON-POROUS SMOOTH VENTRICULAR ASSIST DEVICE CONDUIT

BACKGROUND ART

The present invention is related to methods and apparatus for surgically implantable pumps that provide a mechanical device for augmenting or replacing the blood pumping action of damaged or diseased hearts. More specifically, this invention is related to methods and apparatus for conduits for such pumps to meet the twin requirements of a conduit having a highly non-thrombogenic porous inner surface that is not susceptible to air leakage under negative pressure, whereby the use of such implatable pump procedures is broadly enabled, and wherein the functional utility, ease of use, and wide applicability of the device in medical practice constitutes progress in science and the useful arts. Furthermore, the present invention teaches processes for the use of the device in medical practice.

Of all the cardiovascular disorders, congestive heart failure (CHF) is the only one to show a sharp increase in prevalence since the 1960s. This rise in the number of cases of CHF worldwide is a major and growing public health concern. While the prevalence of coronary heart disease (CHD) has declined in the past few decades and the prevalence of stroke has remained steady until recent years, the number of people suffering from CHF has increased dramatically. In terms of mortality and morbidity, the prognosis for CHF is depressingly poor and in the US, the disease has been recognized as 'epidemic'. The high costs associated with the condition will place an added burden on public health resources as the incidence of CHF continues to rise.

By definition, CHF is a disorder in which the heart fails to pump blood adequately to other organs in the body. This can result in a shortness of breath, fatigue and fluid retention (edema) and if left unchecked can lead to death within a few years. CHF is not a disease per se but a condition that arises as a result of various cardiovascular diseases (CVD). In effect, CHF is the end-stage syndrome of heart muscle disorders and diseases such as hypertension and CHD, which can damage or impair the functionality of the heart and the vessels supplying it.

In the majority of cases, CHF is a progressive condition and over time, the ability of the heart muscle to function properly deteriorates—this process is called cardiac remodeling. As the condition worsens, the ventricular muscle over-stretches and the muscle fails to work to its full efficiency. This leads to a further reduction in the cardiac output and exacerbates symptoms of heart failure.

In CHF, the reduced cardiac output causes a fall in arterial pressure leading to the activation of several compensatory reflexes. The sympathetic nervous system is stimulated, resulting in a direct increase in the force of contraction of the heart and a greater venous return as a response to venoconstriction. Long-term compensation includes the activation of the renin angiotensin system (RAS) and subsequent renal fluid retention. The combined effect of these responses can lead to the formation of edema, especially in the legs and ankles. If heart failure occurs in the left side of the heart, pulmonary edema can result which manifests as breathlessness. In advanced CHF, the severity of the symptoms can be disabling and often leads to hospitalization. An added consideration is sudden cardiac death, which can occur at any time during the course of CHF.

The most common classification of CHF is based on criteria set out by the New York Heart Association (NYHA). Originally published in 1928, the classifications defined the stages of CHF by its clinical severity and the functional status of the cardiac muscle. Over the years the classifications have been updated and the latest revision was in 1994. The NYHA classes of CHF are listed below.

New York Heart Association Functional Classifications of CHF
  Class I Patients with cardiac disease but no resulting limitation of physical activity. No fatigue, palpitations, shortness of breath or angina during normal physical activity.
  Class II Patients with cardiac disease with slight limitation of physical activity. Normal physical activity results in symptoms of heart failure or angina but the patient is comfortable at rest.
  Class III Patients with cardiac disease with marked limitation of physical activity. Slight physical activity results in fatigue, palpitations, shortness of breath or angina but comfortable at rest.
  Class IV Patients with cardiac disease and an inability to carry out physical activity without discomfort. Even at rest, the symptoms of heart failure or angina may be present.

The failing heart is a result of a number of factors combining to reduce the efficiency of the heart as a pump. The most common dysfunction is an impairment of left ventricular function, which is present in 80–90% of patients with CHF. As the blood flow from the heart slows, the blood returning to the heart through the veins can back-up, resulting in congestion in the tissues. This can lead to swelling in the legs and ankle and fluid retention in the lungs, which interferes with breathing and contributes to the characteristic shortness of breath seen in people with CHF.

Several types of surgically implantable pumps have been developed in an effort to provide a mechanical device for augmenting or replacing the blood pumping action of damaged or diseased hearts. Some of these pumps are designed to support single ventricular function. Such pumps usually support the left ventricle, which pumps blood to the entire body except the lungs, since it becomes diseased far more commonly than the right ventricle, which pumps blood only to the lungs. Other devices have been tested and used for providing biventricular function.

Depending on the needs of a particular patient and the design of a pump, pumping units such as so-called "VADs" (ventricular assist devices) can be implanted to assist a functioning heart that does not have adequate pumping capability. Left-ventricular assist devices (LVAD) in particular are recognized as potentially very valuable for assisting patients who suffer from congestive heart failure. An LVAD is able to fully take over the function of the left ventricle, thus perfusing the body with oxygen-rich blood. The LVAD attaches to the patient's natural heart, and to a natural artery, and can be removed if the natural heart recovers. Some LVADs are surgically implanted into the patient's abdominal cavity, while others remain outside the body and are placed in fluid communication with the heart via elongated cannulas. Recently, a National Institutes of Health study estimated that as many as thirty-five thousand people could be candidates for use of a left-ventricular assist device.

At present, conventional ventricular assist devices are used for patients who are waiting for a heart transplant (a so-called, "bridge to transplant"), or alternatively to patients whose natural heart is of such poor condition that the patient cannot be removed from a heart-lung machine without providing some assistance to the patient's heart following otherwise successful open-heart surgery. Still another group of patients eligible for the use of conventional ventricular assist devices are those who suffer massive heart attacks that lead to circulatory collapse. The suitability of long-term utilization of conventional left-ventricular assist devices outside of the clinical environment remains under study.

Expansion and contraction of a variable-volume chamber typically effect blood flow in the LVAD. One-way valves associated with the inflow and outflow ports of the LVAD permit blood flow propelled by the natural left ventricle into the variable-volume chamber during expansion, and blood flow out of this chamber, usually to the ascending thoracic aorta. These one-way flow valves may be constructed as part of the LVAD itself, or may be disposed in separate blood-flow conduits attached thereto. A pair of artificial blood conduits respectively connect the inlet port of the variable-volume chamber (or the inlet end of a valved conduit) to the left ventricle and the outlet port of the variable-volume chamber (or the outlet end of a second valved conduit) to the major artery which is to receive the blood flow from the device.

As is well known, artificial blood conduits have become a valuable tool of modern medicine. One use of such artificial blood conduits is as a temporary or permanent prosthetic artery. Another use is in the connection of temporary blood pumps, such as ventricular assist devices described herein, between the left ventricle of the heart and a major artery.

The demands on artificial blood conduits in ventricular assist devices are great. The conduit must deal with the pulsatile blood flow created by the host's own heart, as well as with the flow, pressure, and pulsations created by the assist device. Moreover, there are differences in flow and pressure between the inflow and outflow conduits connected to the pumping device. For example, while the outflow conduit experiences regular pulses of high pressure, flow in the inflow conduit is dependent on the pumping strength and rhythm of the natural left ventricle on top of which the periodic LVAD pressures are superimposed (i.e., expansion of the variable volume chamber tends to pull fluid from the inflow conduit). The inflow conduit thus sees irregular and typically low flows and pressures; of special importance in the present connection are the negative pressure transients that can occur in the inflow conduit.

Conventional artificial conduits for use in LVADs may be constructed of an elongate flexible woven polyethylene terephthalate fabric tube. In some cases, the conduits are sealed with a thin bio-compatible collagen coating on the inner lumen wall to render the fabric more leak resistant at the time of implantation, and also more compatible with the patient's blood. The collagen coating, typically bovine collagen, eventually is absorbed into the blood stream and is replaced with a natural coating of blood cells, serum protein, and other elements from the blood. In the absence of a sealant, the conduit may have to be pre-clotted by the surgeon just prior to implantation.

As is generally known in the art, a porous surface on the inner lumen wall of an implanted blood conduit is advantageous because it becomes coated with the natural coating of blood cells, serum protein, and other elements from the blood. This coating inhibits clot formation (thrombogenesis) which is highly desirable.

However, such porosity also renders an inflow conduit vulnerable to the entrance of air during the intervals of negative pressure transients that can occur in the inflow conduit as noted above. This raises a serious problem during the surgical implantation of the device which entails operation of the LVAD or VAD during the period when the chest of the patient is open to the atmosphere. During this period, air can be sucked into the inflow conduit during intervals of negative pressure transients as outlined above. This air can lead to air embolisms in the cardiovascular system of the patient undergoing the implantation procedure. Such air embolisms can lead to injury to the patient or even to the death of the patient. It is obvious, therefore, that this risk of air embolisms resulting from the vulnerability of the inflow conduit to the entrance of air during intervals of negative pressure, during implantation of the device in a patient while the chest of the patient is open, is an extremely serious problem. Even if the conduits are sealed with a thin bio-compatible collagen coating on the inner lumen wall to render the fabric more leak resistant at the time of implantation this procedure only addresses the problem of leakage of the lumen contents outward, and does not at all address the problem of the entrance of air during the intervals of negative pressure transients that can occur in the inflow conduit as noted above.

Some non-implantable ventricular assist devices utilize cannula-like conduits that are relatively rigid, some being formed of smooth, reinforced non-porous polyurethane. Such conduits might solve the problem of leakage into the conduit lumen when it is under negative pressure, but they would not be suitable for use in implantable devices, as they will not easily accommodate varying anatomical placements, and tend to kink if bent.

My prior invention of an implantable ventricular assist device disclosed in U.S. Pat. No. 6,001,056, which is expressly incorporated herein in its entirety by reference, comprises an inflow conduit. The inflow conduit includes a flexible tubular graft body having an upstream end and a downstream end, the body having a substantially smooth inner surface for enhanced flow-through of blood with a minimum of surface-induced turbulence. The inflow conduit also includes a ventricular attachment structure to which the upstream end of the body connects, and a coupling fitting on the downstream end of the body. An implantable pumping portion may be placed in flow communication with the inflow conduit and with an outflow conduit. The tubular graft body may be a knitted fabric having a biocompatible sealant impregnated therein, or a closed structured PTFE.

Even in the case of an inflow conduit fabricated from closed structured PTFE in which the tubular wall of the conduit has a pore size of not less than $2\mu$, the water entry pressure for the base tube is still at least about 5 psi. Even when a thin PTFE tape having a thickness of about 0.01 mm and an ethanol bubble point of at least about 2 psi is wrapped about and laminated to the base tube the resulting extremely low porosity tubular wall still leaks air into the lumen of the tube when placed under negative pressure. Thus, even this device does not solve the twin requirements of a conduit having a highly non-thrombogenic porous inner surface that is not susceptible to leakage under negative pressure.

It is therefore readily apparent that in spite of extended efforts in the industry, there remains room for improvement in the construction and function of conduits for ventricular assist devices. Even though conduits for LVAD's are used extensively in medical practice, prior devices, products, or methods available to medical practitioners have not adequately addressed the need for advanced apparatus for conduits for LVAD's to meet the twin requirements of a conduit having a highly non-thrombogenic porous inner surface that is not susceptible to air leakage under negative pressure as set forth above.

The present invention embraces and finally addresses the clear need for advanced apparatus for conduits for LVAD's and VAD's to meet the twin requirements of a conduit having a highly non-thrombogenic porous inner surface that is not susceptible to air leakage under negative pressure as set forth above. Thus, as pioneers and innovators attempt to make methods and apparatus for LVAD's safer, cheaper, more universally used, and of higher quality, none has approached same in combination with simplicity and reliability of operation, until the teachings of the present invention. It is respectfully submitted that other references merely define the state of the art or show the type of systems that have been used to alternately address those issues ameliorated by the teachings of the present invention. Accordingly, further discussions of these references has been omitted at this time due to the fact that they are readily distinguishable from the instant teachings to one of skill in the art.

OBJECTS AND SUMMARY OF THE INVENTION

Accordingly, it is an object of the present invention to provide an advanced conduit for LVAD's that has a highly non-thrombogenic porous inner surface and is not susceptible to air leakage under negative pressure. Another object of the present invention to provide an advanced conduit for LVAD's that has a highly non-thrombogenic porous inner surface and is not susceptible to air leakage under negative pressure that is relatively safe for the patient. Still another object of the present invention to provide an advanced conduit for LVAD's that has a highly non-thrombogenic porous inner surface and is not susceptible to air leakage under negative pressure and is relatively easy to use and comparatively cost-effective to manufacture. Yet still a further object of this invention is to provide an apparatus that is suitable for use with the variety of polymeric materials that are used in LVAD devices. Even still a further object of this invention is to provide a LVAD apparatus that allows the surgical practitioner to operate the apparatus in the open chest of the patient during the implantation procedure. Even yet still a further object of this invention is to provide a LVAD apparatus that allows the surgical practitioner to operate the apparatus in the open chest of the patient during the implantation procedure. Even yet still a further object of this invention is to provide a method for the treatment of congestive heart failure using a LVAD apparatus that allows the surgical practitioner to operate the apparatus in the open chest of the patient during the implantation procedure.

These and other objects are accomplished by the parts, constructions, arrangements, combinations and subcombinations comprising the present invention, the nature of which is set forth in the following general statement, and preferred embodiments of which—illustrative of the best modes in which applicant has contemplated applying the principles—are set forth in the following description and illustrated in the accompanying drawings, and are particularly and distinctly pointed out and set forth in the appended claims forming a part hereof.

BRIEF EXPLANATION OF THE DRAWINGS

The foregoing and other objects and advantages of the invention will be appreciated more fully from the following further description thereof, with reference to the accompanying drawings in which like parts are given like reference numerals and wherein.

DETAILED DESCRIPTION OF THE PREFERRED EMBODIMENTS

Figure 1:
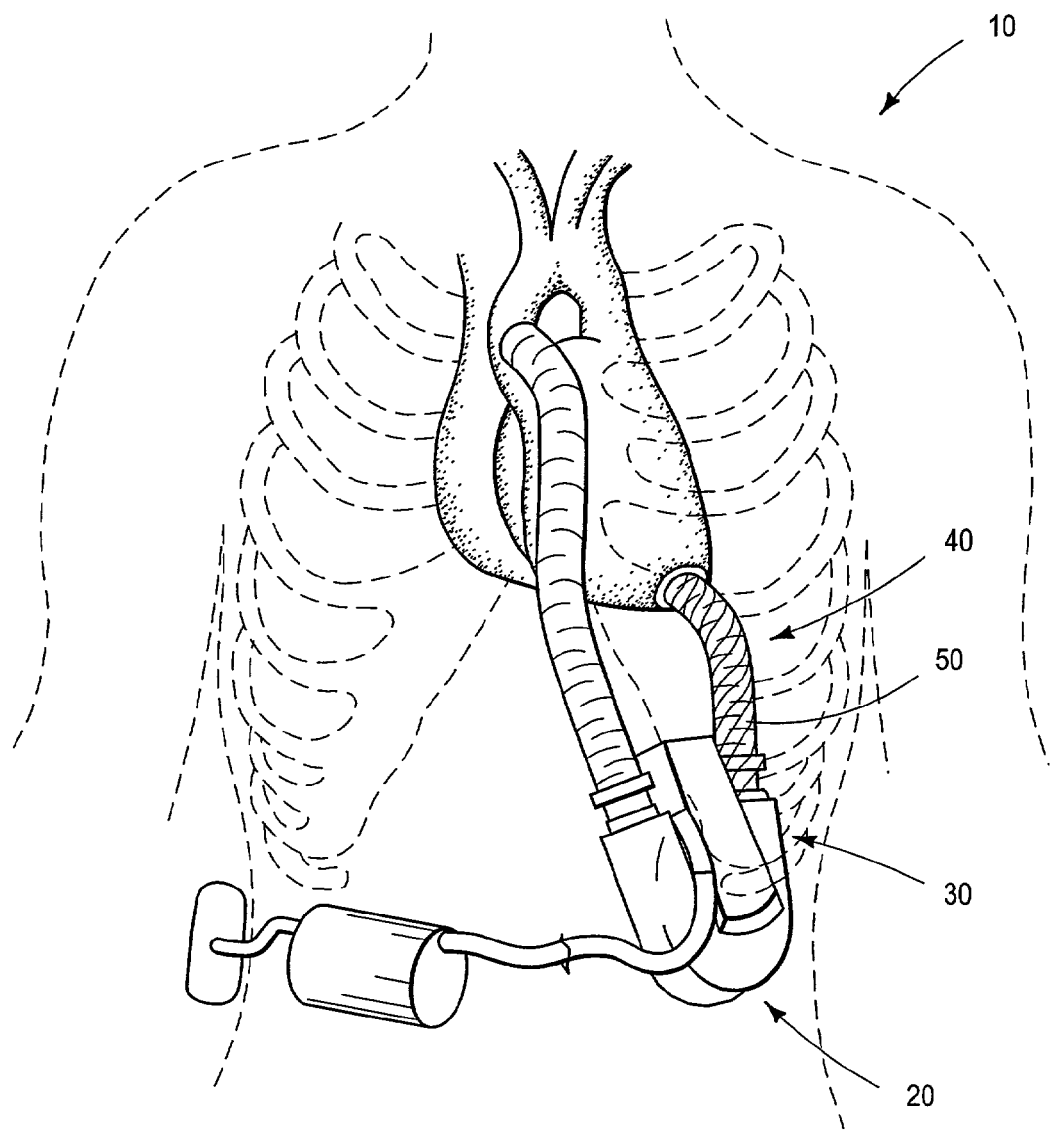
FIG. 1 is a front view of a left ventricular assist system incorporating the present invention connected to the heart of a patient (shown in phantom)

With reference first to FIG. 1, a living human host patient 10 with an open chest is shown in fragmentary front elevational view, and with parts of the patient's anatomy shown in phantom or removed solely for better illustration of the salient features of the present invention. Surgically implanted into the patient is the pumping portion 20 of a ventricular assist device, generally referenced with the numeral 30. The ventricular assist device 30 includes an inflow conduit 40 having a covered flexible porous tubular graft body 50 for communicating blood from the patient's left ventricle into the pumping portion 20. The end of the inflow conduit 40 is connected to the patient's heart by sutures so that blood flow communication is established and maintained.

Figure 2:
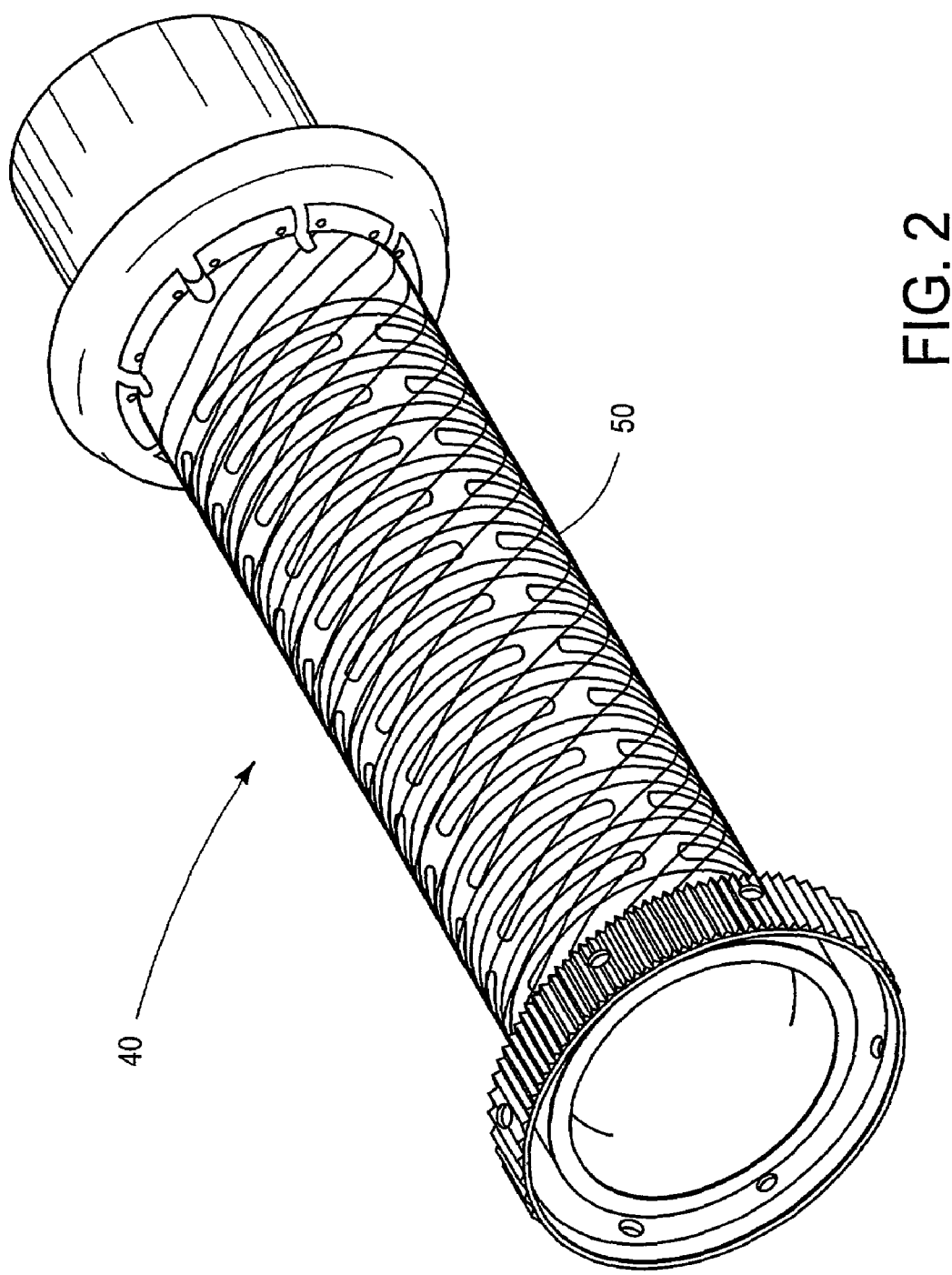
FIG. 2 is a perspective view of an inflow conduit of the present invention.
Figure 3:
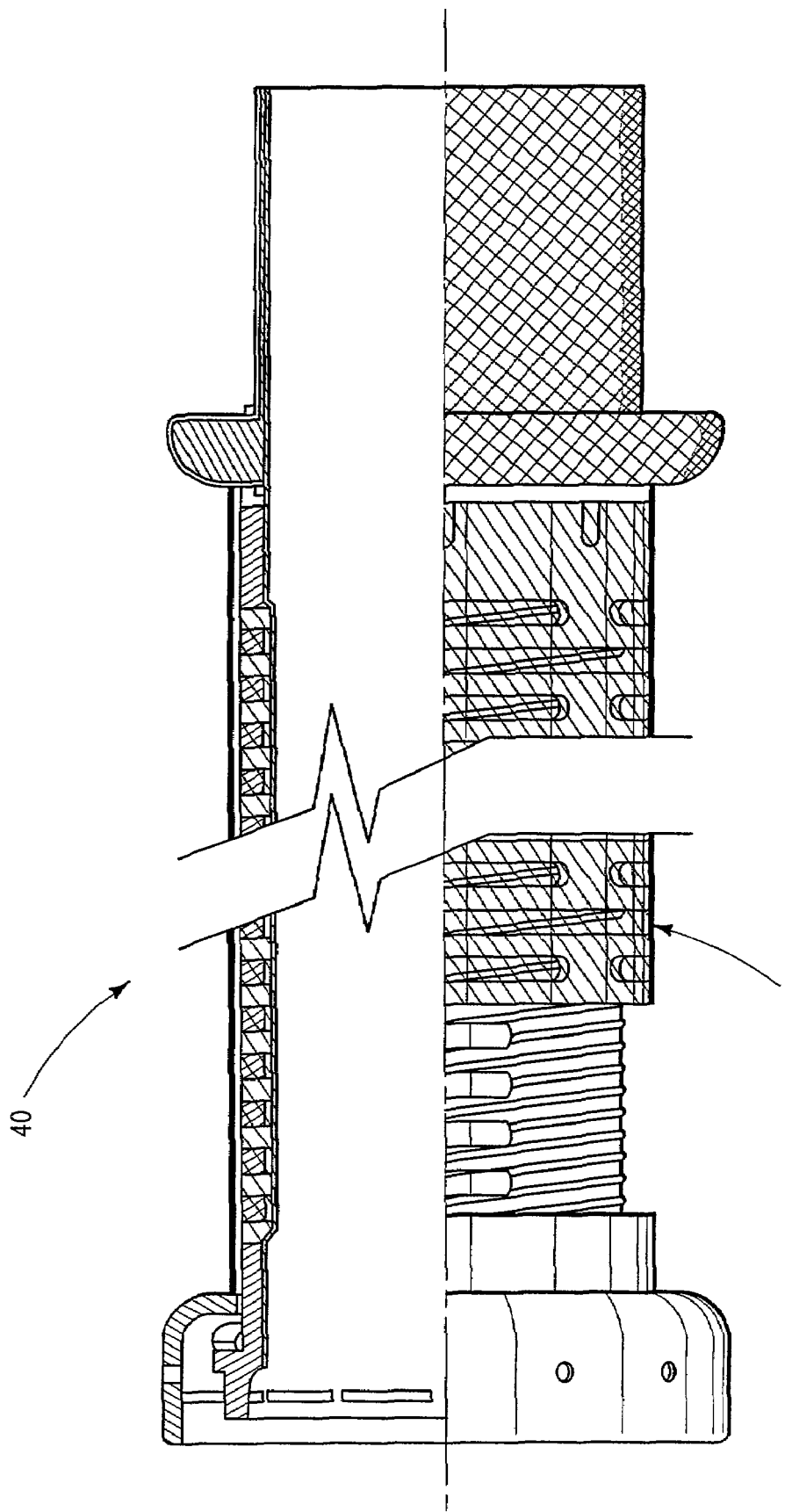
FIG. 3 is a partial sectional view of the inflow conduit of the present invention as shown in FIG. 2 but includes in addition to the embodiment shown in FIG. 2 a coupler fitting.

FIGS. 2 and 3 illustrate a covered flexible porous tubular graft body 50 for inflow conduit 40 (FIG. 1) of ventricular assist device 30.

The present invention is directed to an improved inflow conduit for an implantable ventricular assist device having a flexible, porous tubular graft body that has an upstream end and a downstream end. The tubular graft body has a substantially smooth inner surface for enhanced flow-through of blood with a minimum of surface-induced turbulence, a ventricular attachment structure to which the upstream end of the body connects, and a coupling fitting on the downstream end of the body. The improvement comprises covering the flexible porous tubular graft body with an attached non-porous polymer, whereby a non-porous conduit is formed. The attached non-porous polymer may be attached by thermal bonding, or by a biocompatible adhesive.

The porous tubular graft body of the improved inflow conduit may be fabricated from a biocompatible polymer, for example PTFE or closed structured PTFE, to resist tissue ingrowth from the exterior of the tubular graft body. In the latter inflow conduit, the PTFE may have a pore size of less than about 20$\mu$, or alternatively, less than about 15$\mu$, or again alternatively less than about 2$\mu$. The water entry pressure for the tubular graft body is at least about 5 psi (0.34 atm).

The porous tubular graft body of the improved inflow conduit may be fabricated from further biocompatible polymers such as at least one polymer selected from the group consisting of PTFE, FEP, PFA (perfluoroalkoxy), PPS, PVDF (polyvinylidene fluoride), PEEK, PS/PES, PCTFE, and ETFE. The non-porous polymer used to cover the porous tubular graft body of the improved inflow conduit may be skived, non-porous PTFE tape, skived, non-porous FEP tape, or skived, non-porous tapes made from PFA (perfluoroalkoxy), PPS, PVDF (polyvinylidene fluoride), PEEK, PS/PES, PCTFE, or ETFE. Moreover, the non-porous polymer used to cover the porous tubular graft body of the improved inflow conduit may be vinylidene polymer plastics, polyethylene, polypropylene, polyesters, polyamides, polyethylene terephthalate, high density polyethylene, irradiated polyethylene, polycarbonates, polyurethanes, polyvinyl chloride, polyester copolymers and polyolefin copolymers.

The present invention is also directed to an improved inflow conduit for an implantable ventricular assist device having a flexible, porous tubular graft body that has an upstream end and a downstream end, the body having a substantially smooth inner surface for enhanced flow-through of blood with a minimum of surface-induced turbulence; a ventricular attachment structure to which the upstream end of the body connects; a coupling fitting on the downstream end of the body; an implantable pumping portion in flow communication with the inflow conduit; and an outflow conduit in flow communication with the pumping portion. The improvement comprises covering the flexible porous tubular graft body with an attached non-porous polymer, whereby a non-porous conduit is formed. Implanting this improved implantable ventricular assist device in a patient suffering from congestive heart failure is effective to ameliorate one or more of the symptoms of the heart failure. This improved implantable ventricular assist device may be packaged in packaging material together with a label that indicates that the device is effective for implantation in a patient afflicted with congestive heart failure.

Thus it will be appreciated that the invention provides a new and improved inflow conduit for an implantable ventricular assist device. It should be understood, however, that the foregoing description of the invention is intended merely to be illustrative thereof and that other modifications in embodiments may be apparent to those skilled in the art without departing from its spirit. For example, whereas the invention has been illustrated in connection with an LVAD, it may be used with other VAD's. Additionally, although the illustrative embodiment has been described in connection with an improved PTFE inflow conduit for an implantable ventricular assist device, a properly supported knitted fabric inflow conduit, such as described in my U.S. Pat. No. 6,001,056 could also be used.

On this basis, the instant invention should be recognized as constituting progress in science and the useful arts, and as solving the problems in cardiology enumerated above. In the foregoing description, certain terms have been used for brevity, clearness and understanding, but no unnecessary limitation is to be implied therefrom beyond the requirements of the prior art, because such words are used for descriptive purposes herein and are intended to be broadly construed.

Having described preferred embodiments of the invention with reference to the accompanying drawings, it is to be understood that the invention is not limited to those precise embodiments, and that the various changes and modifications may be effected therein by one skilled in the art without departing from the scope or spirit of the invention s defined in the appended claims. For example, the product can have other shapes, or could make use of other metals and plastics. Thus, the scope of the invention should be determined by the appended claims and their legal equivalents, rather than by the examples given. All changes that come within the meaning and range of equivalency of the claims are to be embraced within their scope.

DEFINITIONS

Unless defined otherwise, all technical and scientific terms used herein have the same meaning as is commonly understood by one of skill in the art to which this invention belongs. All patents and publications referred to herein are incorporated in their entirety by reference.

All abbreviations for fluorocarbon polymers used herein have the same meaning as is commonly understood by one of skill in the art to which this invention belongs. As an example, PTFE refers to polytetrafluoroethylene. As a further example, FEP refers to poly(tetrafluoroethylene-co-hexafluoropropylene). As further examples, the following fluorocarbon polymers are commercially available from Fluorocarbon Company Limited, Caxton Hill, Hertford SG13 7NH, UK: PFA (perfluoroalkoxy), PPS, PVDF (polyvinylidene fluoride), PEEK, PS/PES, PCTFE, and ETFE.

What is claimed is:

1. An inflow conduit for an implantable ventricular assist device comprising:
   a flexible, porous tubular graft body comprising a closed structured biocompatible polytetrafluoroethylene (PTFE) to resist tissue ingrowth having an upstream end and a downstream end, the graft body having a substantially smooth inner surface; and
   a non-porous covering attached on the outside of said flexible, porous tubular graft body,
   whereby said inflow conduit is rendered non-porous.

2. The inflow conduit of claim 1, wherein said non-porous covering is attached to the flexible, porous tubular graft body by thermal bonding.

3. The inflow conduit of claim 1, wherein said non-porous covering is attached to the flexible, porous tubular graft body by a biocompatible adhesive.

4. The inflow conduit of claim 1, wherein said PTFE has a pore size of less than about 20 $\mu$.

5. The inflow conduit of claim 1, wherein said PTFE has a pore size of less than about 15 $\mu$.

6. The inflow conduit of claim 1, wherein said PTFE has a pore size of less than about 2 $\mu$.

7. The inflow conduit of claim 1, wherein the water entry pressure for said flexible, tubular graft body is at least about 5 psi (0.34 atm).

8. An implantable ventricular assist device comprising:
   an inflow conduit comprising a flexible, porous tubular graft body having an upstream end and a downstream end, the body having a substantially smooth inner surface for enhanced flow-through of blood with a minimum of surface-induced turbulence; a ventricular attachment structure connected to the upstream end of the flexible, porous tubular graft body; a coupling fitting connected to the downstream end of the flexible, porous tubular graft body;
   an implantable pumping portion in flow communication with said inflow conduit;
   an outflow conduit in flow communication with said implantable pumping portion; and
   a non-porous covering comprising a polymer attached on the outside of said flexible, porous tubular graft body, whereby said inflow conduit is rendered non-porous.

9. A method for the treatment of congestive heart failure, comprising
   implanting the device of claim 8 in a patient in need of such treatment wherein said implantation is effective to ameliorate one or more of the symptoms of said heart failure.

10. An inflow conduit for an implantable ventricular assist device comprising:
    a flexible, porous tubular graft body having a lumen, an upstream end and a downstream end, the graft body having a substantially smooth inner surface; and
    a covering attached on the outside of the tubular graft body that will not leak air therethrough when the lumen of the tubular graft body is placed under negative pressures present in ventricular assist device inflow conduits.

11. The inflow conduit of claim 10, wherein the tubular graft body comprises a biocompatible polymer.

12. The inflow conduit of claim 11, wherein the biocompatible polymer is polytetrafluoroethylene (PTFE).

13. The inflow conduit of claim 12, wherein the PTFE is closed structured to resist tissue ingrowth.

14. The inflow conduit of claim 13, wherein the PTFE has a pore size of less than about 20 $\mu$.

15. The inflow conduit of claim 14, wherein the biocompatible polymer is fluorinated ethylene propylene (FEP).

16. The inflow conduit of claim 10, wherein the water entry pressure for the tubular graft body is at least about 5 psi (0.34 atm).

17. The inflow conduit of claim 10, wherein the tubular graft body comprises at least one polymer selected from the group consisting of PTFE, FEP, perfluoroalkoxy (PFA), polyphenylenesulfide (PPS), polyvinylidene fluoride (PVDF), polyetheretherketone (PEEK), polystyrene/polyethylstyrene (PS/PES), polychlorotetrafluoroethylene (PCTFE), and ethylenetetrafluoroethylene (ETFE).

18. The inflow conduit of claim 10, wherein the covering is non-porous.

19. The inflow conduit of claim 10, wherein the covering comprises a PTFE tape.

20. The inflow conduit of claim 10, wherein the covering comprises an FEP tape.

21. The inflow conduit of claim 10, wherein the covering comprises a polymer tape selected from the group consisting of PEA, PPS, PVDF, PEEK, PS/PES, PCTFE, and ETFE.

22. The inflow conduit of claim 10, wherein the covering comprises a polymer selected from the group consisting of vinylidene polymer plastics, polyethylene, polypropylene, polyesters, polyamides, polyethylene terephthalate, high density polyethylene, irradiated polyethylene, polycarbonates, polyurethanes, polyvinyl chloride, polyester copolymers and polyolefin copolymers.

23. The inflow conduit of claim 10, wherein the covering is attached to the tubular graft body by thermal bonding.

24. The inflow conduit of claim 10, wherein the covering is attached to the tubular graft body by a biocompatible adhesive.

25. An inflow conduit for an implantable ventricular assist device comprising:
   a flexible, porous tubular graft body having an upstream end and a downstream end, the graft body having a substantially smooth inner surface; and
   a non-porous covering comprising a non-porous PTFE tape attached on the outside of said flexible, porous tubular graft body,
   whereby said inflow conduit is rendered non-porous.

26. An inflow conduit for an implantable ventricular assist device comprising:
   a flexible, porous tubular graft body having an upstream end and a downstream end, the graft body having a substantially smooth inner surface; and
   a non-porous covering comprising a non-porous FEP tape attached on the outside of said flexible, porous tubular graft body,
   whereby said inflow conduit is rendered non-porous.

27. An inflow conduit for an implantable ventricular assist device comprising:
   a flexible, porous tubular graft body having an upstream end and a downstream end, the graft body having a substantially smooth inner surface; and
   a non-porous covering comprising a non-porous polymer tape selected from the group consisting of PFA, PPS, PVDF, PEEK, PS/PES, PCTFE, and ETFE, attached on the outside of said flexible, porous tubular graft body,
   whereby said inflow conduit is rendered non-porous.

* * * * *